United States Patent [19]

Barany

[11] Patent Number: 5,306,562
[45] Date of Patent: Apr. 26, 1994

[54] XANTHENYLAMIDE HANDLE FOR USE IN PEPTIDE SYNTHESIS

[75] Inventor: George Barany, Falcon Heights, Minn.

[73] Assignee: Regents of the University of Minnesota, Minneapolis, Minn.

[21] Appl. No.: 884,653

[22] Filed: May 15, 1992

Related U.S. Application Data

[63] Continuation-in-part of Ser. No. 576,232, Aug. 31, 1990, Pat. No. 5,117,009.

[51] Int. Cl.$^5$ .............. B32B 5/16; C08F 8/00; C08F 2/00; C07D 231/00
[52] U.S. Cl. ................... 428/402; 525/132; 526/72; 548/364.4; 548/371.1; 549/394
[58] Field of Search .............. 549/394; 548/364, 358; 526/72; 525/132; 428/402

[56] References Cited

FOREIGN PATENT DOCUMENTS

19697A/90  5/1990  Italy .

OTHER PUBLICATIONS

Albericio, F. et al., *J. Organ. Chem.* 55:3730–3743 (1990).
P. Sieber, *Tetrahedron Letters* 28:2107–2110 (1987).
Barany et al., *Int. J. Peptide Protein Res.* 30:703–739 (1987).
Caciagli, V. et al., *Proceeding of the European Peptide Symposium* (Sep. 1990), Abstract P97.
European Search Report for EP 91307876.2.
Patrick et al., *Chemical Abstracts* 79:78525a (Oct. 1, 1973).
Capuano et al., *Chemical Abstracts* 76:85648j (Apr. 10, 1972).
Bender et al., *Chemical Abstracts* 99:88276A (Sep. 5, 1983).

*Primary Examiner*—John Kight, III
*Assistant Examiner*—T. Mosley
*Attorney, Agent, or Firm*—Hamiltion, Brook, Smith & Reynolds

[57] ABSTRACT

The preparation and properties of xanthenylamide handles for use in peptide synthesis is disclosed. The compounds, omega-(9-(9-fluorenylmethyloxycarbonyl)aminoxanthan-2-oxy)alkanoic acid derivatives, are used as peptide handles in the solid-phase synthesis of peptide amides.

6 Claims, 3 Drawing Sheets

XANTHENYLAMIDE HANDLE FOR USE IN PEPTIDE SYNTHESIS

RELATED APPLICATION

This is a continuation-in-part of U.S. Patent application Ser. No. 07/576,232, filed Aug. 31, 1990, now U.S. Pat. No. 5,117,009, the entire teachings of which are incorporated herein by reference.

BACKGROUND OF THE INVENTION

A number of naturally occurring peptides, including oxytocin, secretin, apamin, and several releasing hormones from the brain, are peptide amides, that is, they contain an amide function at the carboxyl terminal. The synthesis of C-terminal peptide amides can be problematical because of the acid-sensitivity of some of these peptides, and the tendency of some amino acid residues, such as tryptophan, to become alkylated under the conditions used in most synthesis methods. The synthesis of peptide amides by solid-phase synthesis has most commonly involved releasing the peptide amide from the solid phase using either a strong acid (e.g., anhydrous hydrogen fluoride) or a strong base (e.g., ammonia) for final cleavage. For example, ammonolysis of benzyl and other ester anchoring linkages has been used, or benzhydrylamine support resins have been applied in conjunction with protection strategies that use anhydrous hydrogen fluoride (HF) for the final cleavage of the peptide from the support. Such harsh conditions can cause undesirable side reactions. G. Barany and R. B. Merrifield, *In: The Peptides,* E. Gross and J. Meienhofer (eds.), Vol. 2, pp. 1–284, Academic Press, New York (1979).

Several drawbacks to these methods exist. For example, ammonolysis of sterically hindered amino acids, such as valine, proceeds very slowly, and is even further retarded with the increasing length of the peptide chain. In addition, this technique is limited to peptides lacking $C^\omega$-benzyl-protected aspartate or glutamate residues, which would be vulnerable to attack by ammonia. Finally, prolonged treatment with ammonia leads to partial racemization of Cys(Acm) residues. Numerous difficulties have been documented as well, which accompany cleavage with strong acids, such as HF.

Solutions which have been proposed for these problems include milder conditions and orthogonal protection schemes. An "orthogonal" system is defined as one using two or more independent classes of protecting groups which are removed by different chemical mechanisms. The most flexible approach for the solid-phase synthesis of peptide amides appears to involve the use in orthogonal systems of handles which incorporate a precursor of the amide function. These handles are coupled onto amine-functionalized solid supports and serve as a starting point for peptide chain elongation. For example, handles which are useful for anchoring tert-butyloxycarbonyl (Boc)-protected amino acids to solid supports are described by Gaehde and Matsueda in *Int. J. Peptide Protein Res., 1* 18:451 (1981). Albericio and Barany describe handles for use with Fmoc-protected amino acids. F. Albericio and G. Barany, *Int. J. Peptide Protein Res.,* 30:206–216 (1987); Albericio et al., *J. Organic Chemistry,* 55:3730–3743 (1990). However, the synthesis and/or cleavage conditions used in the referenced methods are too harsh for some peptide amides. A handle which allows acid-sensitive peptide amides to be efficiently produced and cleaved from the support under mild conditions would be valuable.

SUMMARY OF THE INVENTION

The invention relates to novel compounds which can be used as handles for linking protected amino acids or peptides to a support during peptide synthesis. The compounds are Fmoc-xanthenylamide derivatives having the general formula:

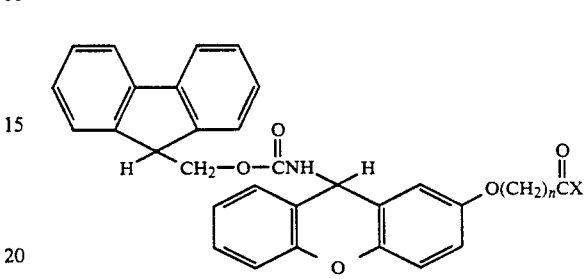

wherein n is an integer of from about 1 to about 10; and wherein X is OH or the activating group of an active ester or thioester. The compounds are used as handles for amino acids or peptides during solid-phase peptide synthesis, in which they are linked to an amino-functionalized solid support or to an amino group of a spacer arm attached to a solid support. When the compounds are attached to the solid support, X represents the amino component of the amide linkage to the amino-functionalized support. The present compounds, which are omega-(9-(9-fluorenylmethyloxycarbonyl)aminoxanthen-2-oxy)alkanoic acid derivatives, are particularly useful for synthesizing peptides or proteins having amide groups in the C-terminal position.

A method of preparing the present Fmoc-xanthenylamide compounds is also the subject of the present invention. The method involves alkylating 2-hydroxyxanthone with appropriate ω-halo acids or esters. The resulting intermediate is then reduced to yield the xanthydrol intermediate, which is then reacted with 9-fluorenylmethyl carbamate (Fmoc-NH₂) to yield the present xanthenylamide derivatives.

A method of synthesizing peptides or proteins utilizing the present compounds is also the subject of the present invention. In this method, the present compounds are attached to a solid resin or support, or to an amino group on a spacer arm attached to the solid support. The xanthenyl compound reacts through its side-chain free or activated carboxyl group (represented by X) with the amino group, forming a stable amide linkage. This resin-linked amino acid or peptide amide serves as the starting point for chain elongation. The Fmoc group is removed and a first amino acid or peptide is attached to the xanthenylamine of the handle, forming a C-terminal amide bond. Subsequent amino acid residues are coupled by standard solid-phase synthesis procedures.

The present Fmoc-xanthenyl compounds and method of using them in solid-phase peptide synthesis have several advantages. Cleavage of the finished peptide or protein from the xanthenyl handle occurs under mild acid conditions, which allows direct preparation of acid-sensitive conjugates. Undesirable side reactions are minimized using the present compounds and method.

DETAILED DESCRIPTION OF THE INVENTION

The present Fmoc-xanthenylamide compounds have the following general formula:

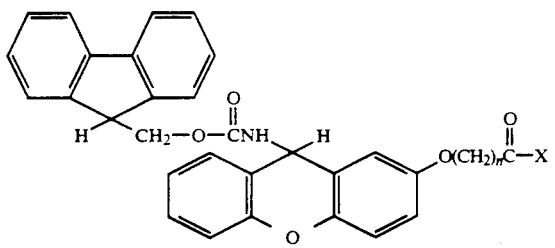

wherein n is an integer of from about 1 to about 10 and wherein X is OH, or the activating group of an active ester or thioester. X also represents the amino component of an amide linkage when the compound is attached to an amino-functionalized solid support. The term "active ester" refers to compounds which activate carboxyl groups to make them undergo more ready reactions with amino groups on the support or on another amino acid or peptide. Activating groups which can be used in the present invention include, for example, trichlorophenyl (TCP) esters, pentafluorophenyl (PFP) esters, pentachlorophenyl (PCP) esters and methyl phenylpyrazolinone (Mpp) esters.

Figure 1:
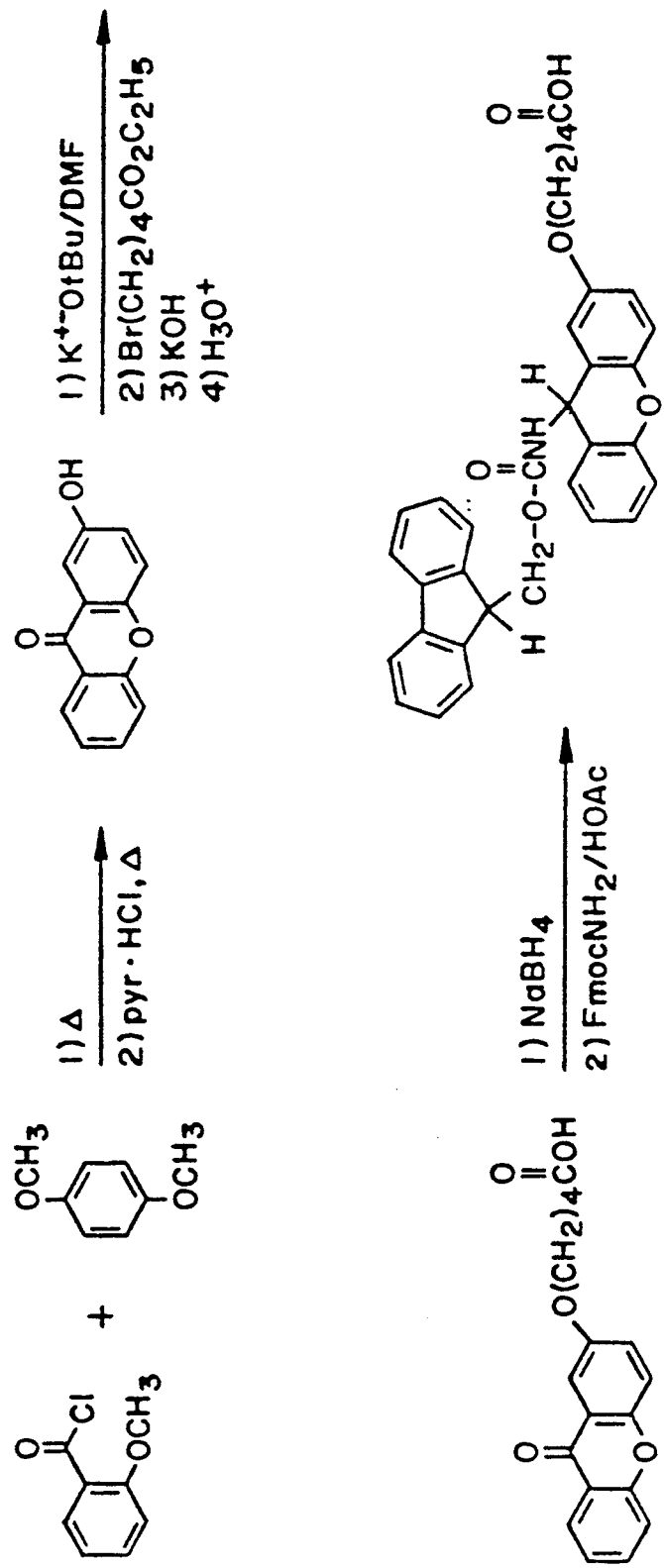
FIG. 1 is a schematic illustration of the synthesis of 5-(9-(9-fluorenylmethyloxycarbonyl)aminoxanthen-2-oxy)valeric acid.

The present xanthenyl compounds are generally known as omega-(9-(9-fluorenylmethyloxycarbonyl)aminoxanthen-2-oxy)alkanoic acid. The compounds are prepared from 2-hydroxyxanthone, as described in the procedures set forth in the Example Section. 2-Hydroxyxanthone is alkylated with appropriate ω-halo acids or esters to introduce the eventual handle sidechain. The present method provides a successful route to generate a xanthydrol and trap it with Fmoc-amide, as illustrated in FIG. 1 for the 2-valeryl derivative (wherein n=4, and X is OH). The same chemistry can be carried out also for other derivatives, e.g., the 2-oxyacetyl derivative.

The xanthenyl handle is attached to amino-functionalized supports or to the amine groups of spacer arms attached to solid supports. The present Fmoc-xanthenyl compounds react through their side chain carboxyl groups with amino groups, forming stable amide linkages. The reaction can be performed using standard coupling methods for creation of amide linkages, for example, N,N'-dicyclohexylcarbodiimide (DCC) or N,N'-diisopropylcarbodiimide (DIPCDI) plus 1-hydroxybenzotriazole (HOBt) coupling. See, F. Albericio et al., *J. Organic Chem.*, 55:3730–3743 (1990) the teachings of which are hereby incorporated herein by reference. Other known techniques can be used, such as BOP/HOBt/NMM. The present compounds are attached by reacting a slight excess of the present xanthenyl compounds for each equivalent of amino groups present on the support.

A variety of amino-functionalized supports can be used as the solid phase, for example, macromolecules or solids, such as membranes, porous glass, silica, polystyrenes, polydimethylacrylamides, cotton or paper. Functionalized polystyrene resins, such as amino-functionalized polystyrene, aminomethyl polystyrene, aminoacyl polystyrene, or p-methylbenzhydrylamine polystyrene resins can be used for this purpose. Polyethylene glycol-polystyrene (PEG-PS) graft co-polymers functionalized with amino groups are particularly useful solid-phases. PEG-PS resins which can be used are described for example in co-pending U.S. application Ser. No. 07/576,314 (filed Aug. 31, 1990) and 07/715,289 (filed Jun. 14, 1991), both entitled "Polyethylene Glycol Derivatives For Solid-Phase Applications" by Barany et al., the teachings of each are incorporated herein by reference.

The resulting resin-linked handle is then reacted with a C-terminal amino acid or peptide which serves as the starting point for chain elongation. The amino acid or peptide is coupled to the handle according to the following procedure. The Fmoc group on the xanthenyl handle is first removed, for example, using piperidine/N,N-dimethylformamide (3:7), and the resulting amino group is acylated with the C-terminal α-carboxyl group of an $N^\alpha$-protected amino acid or peptide by a standard method for creating amide linkages, such as DCC-mediated coupling. Other coupling methods can be used. The resulting solid-phase, having attached thereto the amino acid or peptide through the xanthenyl handle of the present invention, is ready for use in synthesizing a peptide or protein.

The first amino acid or peptide can also be coupled to the handle prior to attaching the handle to the solid support, using the coupling methods described above.

The resulting amino acid/peptide-handle-resin complex provides a well-defined starting structure for peptide chain elongation. Solid-phase peptide synthesis can then be carried out by standard methods for synthesizing peptide amides. Solid-phase synthesis typically begins with covalent attachment of the α-carboxyl end of an $N^\alpha$-protected amino acid to the amino acid or peptide linked to the handle. The synthesis cycle generally consists of deprotection of the α-amino group of the amino acid, washing, and, if necessary, a neutralization step, followed by reaction with a carboxyl-activated form of the next $N^\alpha$-protected amino acid. The cycle is repeated to form the peptide or protein of interest. Solid-phase synthesis methods for peptide amides which can be used with the present xanthenyl handles include, for example, methods described by Albericio et al., *J.Org. Chem.*, 55:3730–3743 (1990); the teachings of which are hereby incorporated herein by reference.

Peptide synthesis using a solid support containing the present xanthenyl handles proceeds well, and final cleavage from the support is accomplished with a mild acid, such as dilute trifluoroacetic acid (TFA). TFA having a concentration of from about 3% to about 25% is useful in the present method, for example. The presence of at least four carbon atoms at the carboxyl end of the present derivatives is preferred. The presence of a four-carbon spacer in the valeryl derivative (where n=4), for example, leads to a 5-fold increase in acid lability over the corresponding analog having a one-carbon spacer (where n=1). It is even possible to release peptide amides made using the preferred xanthenyl compound (having a 4-carbon spacer, i.e., where n=4) with partial retention of side-chain tert-butyl protection.

In contradistinction to experiences with other handles, scavengers such as dimethyl sulfide, 1,2-ethanedithiol, anisole, thioanisole, and/or tri(isopropyl)silane are not required for high cleavage yields, nor for the optimal purity of tryptophan-containing peptides.

The handles of the present invention and methods of using them provide an efficient synthesis for peptide amides which are difficult to produce by other methods. For example, peptides containing tryptophan and/or tyrosine sulfate residues can be successfully made using the present compounds and methods. The method avoids the use of strong acids or bases and maximizes the yields and purities of the desired peptides which are obtained. In particular, the present handles provide excellent yields of tryptophan and tyrosine sulfate-containing peptide amides.

The invention will now be further illustrated by the following examples:

Exemplification

EXAMPLE 1:

Preparation of 5-(9-(9-Fluorenylmethyloxycarbonyl-)aminoxanthen-2-oxy) acetic Acid 2,2',5-Trimethoxybenzophenone Method A A mixture of o-anisoyl chloride (21.8 mL, 0.147 mol) and 1,4-dimethoxybenzene (37.2 g, 0.27 mol) was heated under $N_2$ for 20 hours at 200° C. (bath). Distillation after HCl evolution subsided led to recovery of 1,4-dimethoxybenzene (18.7 g), b.p. 92°–95° C. (8 mm) followed by the title product, shown below. Yield: 25.4 g (63%). b.p. 232° C. (7 mm). An NMR-pure oil was suitable for carrying forward to the next step.

Method B

A mixture of o-anisoyl chloride (39 mL, 0.26 mol) and carbon disulfide (53 mL) was added dropwise over 2 h under ambient conditions to a stirred mixture of 1,4-dimethoxybenzene (75 g, 0.54 mol, soluble) and anhydrous aluminum trichloride (46.0 g, 0.35 mol, suspended) in carbon disulfide (95 mL). Reaction was accompanied by vigorous HCl evolution, and a modest spontaneous exotherm. After 4 hours, the mixture was quenched by pouring into a mixture of ice (1 kg) and 12 N aqueous HCl (10 mL). The organic layer was washed with aqueous saturated NaCl (1 L), water (2×1), and again with aqueous saturated NaCl (1 L), dried ($Na_2SO_4$), and distilled to give recovered 1,4-dimethoxybenzene (16.8 g), followed by the title product. Yield: 61 g (85%).

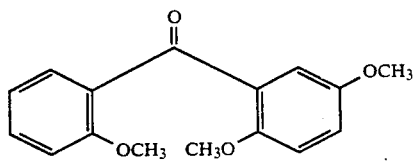

2-Hydroxyxanthone

A mixture of crude 2,2',5-trimethoxybenzophenone (22.6 g, 83 mmol) prepared as described above, and pyridine hydrochloride (121 g, 1.04 mol) was refluxed (~210° C.) for 10 hours under $N_2$. The mixture was then poured into ice water (350 g), and the resultant yellow-green precipitate was collected by filtration and washed with water (2×100 mL), and 6 N aqueous HCl (3×100 mL), and dried in vacuo. Yield: 14.1 g (80%). TLC: $R_f$ 0.54 [benzene-EtOH (20:3)]. m.p. 245°–246° C. NMR data in accordance with structure.

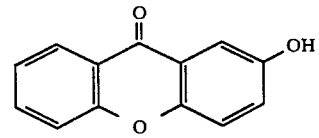

Ethyl (9-Oxoxanthen-2-oxy)acetate

A mixture of 2-hydroxyanthone (14.1 g, 66 mmol) prepared as described above, ethyl bromoacetate (14.5 mL, 0.13 mol), and anhydrous potassium carbonate (53 g, 0.38 mol) in acetone (350 mL) plus DMF (12 mL) was refluxed for 6 hours. The cooled reaction mixture was filtered to remove inorganic salts, washed with acetone (3×50 mL) and ether (3×50 mL), concentrated, and placed under hexane, whereupon crystals formed. Yield: 16.1 g (82%), TLC: $R_f$ 0.81 [one spot, benzen-EtOH (20:3)], m.p. 96°–98° C. NMR data and elemental analysis in accordance with structure.

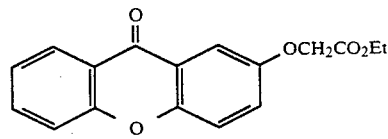

(9-Oxoxanthen-2-oxy)acetic Acid, Potassium Salt and Free Acid

Ethyl (9-oxoxanthen-2-oxyacetate (10 g, 33 mmol) prepared as described above, was dissolved in 95% ethanol (150 mL), and 4 N aqueous KOH (30 mL, 0.12 mol) and water (15 mL) were added. The mixture was stirred for 35 minutes at 35°–40° C., cooled, and the solid precipitate which formed was collected by filtration, washed with absolute ether (3'20 mL), and air-dried. The structure of the potassium salt is shown below. Yield: 9.25 g (96%). TLC, $R_f$ 0.90 [MeOH-$H_2O$(4:1)]. NMR data in accordance with structure.

The potassium salt formed as above was used directly in the next reaction. However, for further characterization, a portion was converted to the free acid by dissolving in water and acidification (to pH1) with 12 N HCl. The free acid had a meltinq point of 179°–182° C.

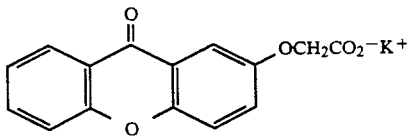

(9-Hydroxyxanthen-2-oxy)acetate, Mixture Sodium/-Potassium Salts

A solution of potassium (9-oxoxanthen-2-oxy)acetate (8.48 g, 27.5 mmol) prepared as described above, in water (70 mL) was treated with sodium borohydride (2.0 g, 52.8 mmol) which was added in small portions over 1.5 hours while stirring. After 20 hours at 25° C., further sodium borohydride (1.0 g, 26.4 mmol) was added, and reduction was continued for 26 hours at 25° C. The resultant white precipitate was filtered, washed with EtOH (3×50 mL), combined with a second crop which appeared after partial concentration oft he mother liquor, and air-dried. Yield: 7.2 g (89%); TLC $R_f=0.22$, [EtOH-H$_2$O-EtOAc (12:1:1); major spot shich became yellow after spraying with 2% CF$_3$COOH in CH$_2$Cl$_2$]. NMR data in accordance with structure.

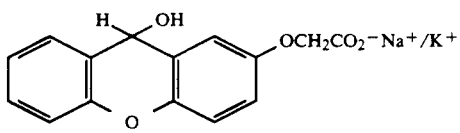

5-(9-(9-Fluorenylmethyloxycarbonyl)aminoxanthen-2-Oxy)acetic Acid

A solution of Fmoc-amide (0.91 g, 3.6 mmol) in glacial acetic acid (30 mL) was added to a solution of the (9-hydroxyxanthen-2-oxy)acetate salt mixture (1.0 g, 3.3 mmol), prepared as described above, in acetic acid (55 mL). Next a solution of p-toluenesulfonic acid (0.1 g, 0.5 mmol) in acetic acid (10 mL) was added over 20 minutes, and the reaction mixture was stirred for 24 hours. The product slowly precipitated as a white solid, which was filtered, washed with water (4×10 mL), and dried in vacuo over P$_2$O$_5$. Yield: 1.34 g (83%). TLC pure, $R_f$: 0.54 (acetone/EtOH/H$_2$O 12:1:1). NMR data and elemental analysis in accordance with structure.

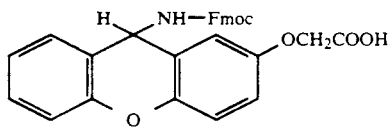

EXAMPLE 2

Preparation of 5-(9-(9-Fluorenylmethyloxyxcarbonyl) aminoxanthen-2-oxyvaleric Acid Ethyl 5-9-Oxoxanthen-2-oxy)valerate 2-hydroxyxanthone (7.7 g, 36 mmol), prepared as described in Example 1, was dissolved in DMF (50 mL), and potassium tert-butoxide (4.6 g, 41 mmol) was added in one portion. The mixture was stirred under N$_2$ at 25° C. for 1 hour, and then a solution of ethyl 5-bromovalerate (7.1 mL, 42 mmol) in DMF (20 mL) was added dropwise over 20 minutes. The reaction mixture was heated at 115° C. for 11 hours, then cooled, filtered, and washed with EtOAc (2×10 mL). The filtrate was concentrated to provide a light-brown oily residue, which slowly solidified at room temperature. Light-beige crystals were collected and washed with n-hexane (3×10 mL). TLC pure, $R_f=0.79$ (benzene-EtOH 10:9). Yield: 9.70 g (79%). A small amount of the product was recrystallized from n-hexane-EtOH (10:1) for elemental analysis which was in accordance with theoretical. White needles, m.p. 58°-59° C. NMR data in accordance with structure.

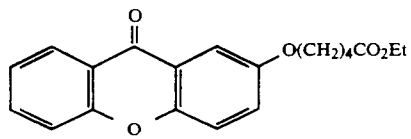

5-(9-Oxoxanthen-2-oxy)valeric Acid

Ethyl 5-(9-oxoxanthen-2-oxy)valerate (7.0 g, 21 mmol) prepared as described above was suspended in 95% EtOH (50 mL), and 4 N aqueous NaOH (50 mL, 0.2 mmol) was added. The reaction mixture was homogeneous within 1h, and saponification proceeded at 25° C. for a total of 4 h. Subsequently, 12 N aqueous HCl (17 mL) was added with cooling to adjust the pH to 3. A light-gray precipitate formed, which was collected, washed with water (3×10 mL), and dried in vacuo over P$_2$O$_5$, to give the free acid product. Yield: 6.1 g (94%). A small amount of the product was recrystallized from n-hexane-EtOH (10:1) for elemental analysis in accordance with structure. Light beige needles, m.p. 151-152° C.

NMR data in accordance with structure.

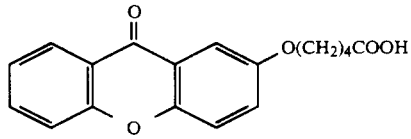

5-(9-Hydroxyxanthen-2-oxy)valeric Acid

Aqueous NaOH (9 mL, 1 N, 9 mmol) was added dropwise to adjust a solution of 5-(9-oxoxanthen-2-oxy)-valeric acid (2.5 g, 8.0 mmol), prepared as described above, in water (60 mL) to a pH of 8. Sodium borohydride (2.5 g, 66 mmol) was added in small portions over 15 min. The mixture was stirred at 50° C. for 3 hours (TLC showed no starting ketone), and then acetone (60 mL) was added carefully to decompose excess sodium borohydride. The mixture was partially concentrated (to ~70 mL) in vacuo at 25° C., and the remaining aqueous solution added dropwise to a well-stirred mixture of ice-water (40 mL) and glacial acetic acid (30 mL). The immediate precipitate was collected, washed with water (3×20 mL) and anhydrous ether (2×20 ml) and dried in vacuo over P$_2$O$_5$ to give a white powder. Yield: 2.4 g(97%). There was a very small amount of by-product ($R_f=0.02$) in TLC; the main product $R_f=0.51$; [EtoAc-MeOH(2:1) major spot which became yellow after spraying with TFA-CH$_2$Cl$_2$ (1:19) at 25° C.], 0.02 minor impurity. NMR data in accordance with structure.

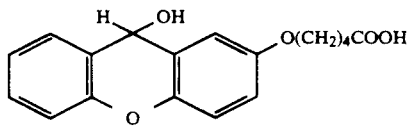

5-(9-(9-Fluorenylmethyloxycarbonyl)aminoxanthen-2-oxy)valeric Acid

A solution of p-toluenesulfonic acid (0.15 g, 0.8 mmol) in glacial acetic acid (3 mL) was added dropwise at 25° C. over 15 minutes to a well-stirred suspsension of 5-(9-hydroxy-xanthen-2-oxy)valeric acid (2.0 g, 6.4 mmol) prepared as described above and Fmoc-amide (1.84 g, 8.2 mmol) in glacial acetic acid (50 mL). This mixture was stirred continuously and then filtered after 3 hours to collect a white solid which was washed with water (3×20 mL) and ehtyl ether (3×20 mL). The solid was dried in vacuo over $P_2O_5$ at 25° C. Yield: 2.35 g(61%, m.p. 210–211° C., $R_f$: 0.53 EtOAc/MeOh 5:1. NMR data and elemental analysis in accordance with structure.

EXAMPLE 3

Preparation of Tabanus Peptide

An octapeptide derived from *Tabanus atratus*, the tabanus adipokinetic hormone peptide, was synthesized using the 5-(9-(9-fluorenylmethyloxycarbonyl)aminoxanthen-2-oxy)valeric acid (Fmoc-XAL) handle attached to a PEG-PS solid support. This octapeptide, which has the sequence:

pGlu-Leu-Thr-Phe-Thr-Pro-Gly-Trp-NH$_2$ is difficult to synthesize by most solid phase synthesis methods due to the presence of the tryptophan amide moiety, which is prone to alkylation.

Figure 2:
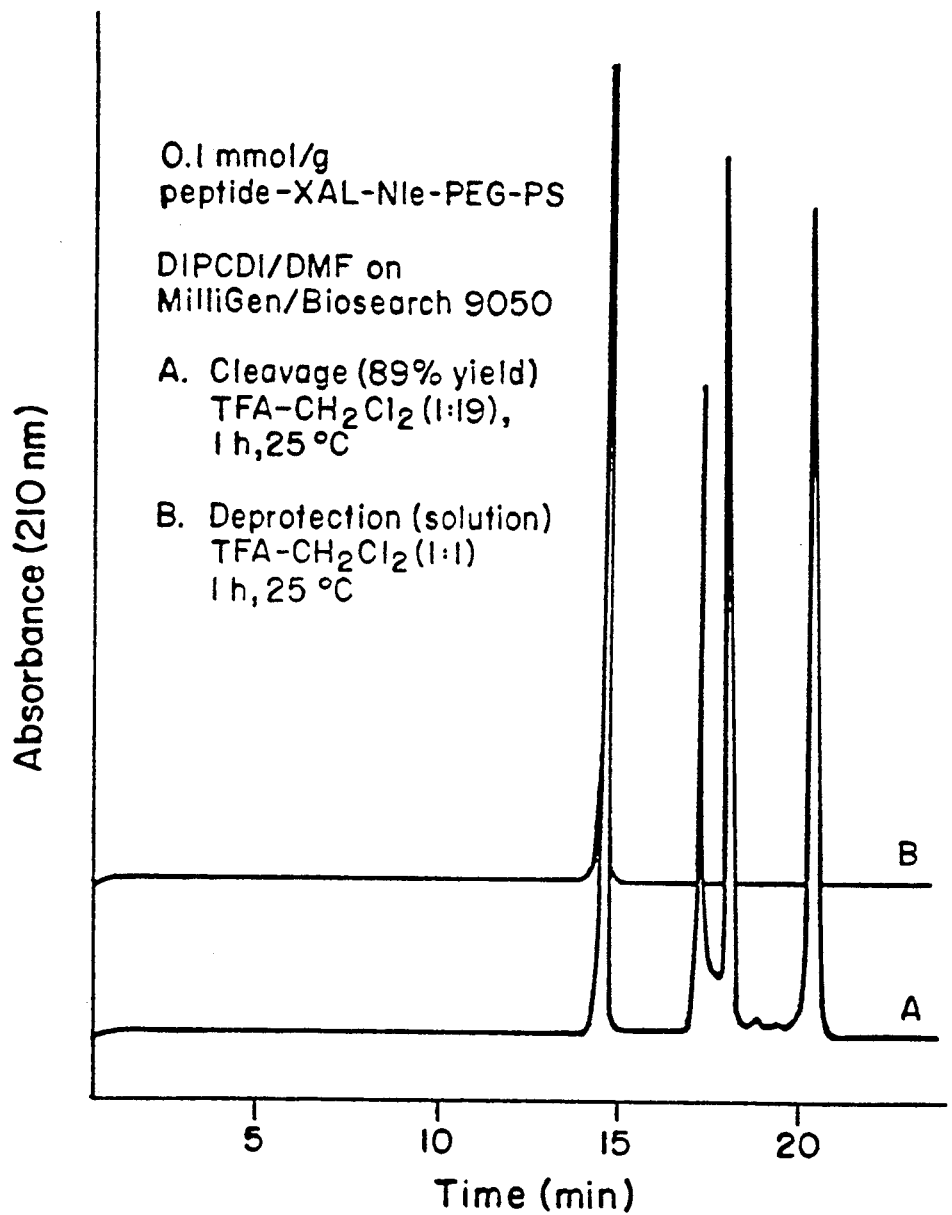
FIG. 2 is an HPLC chromatogram illustrating the results obtained synthesizing Tabanus Adipokinetic Hormone using the XAL handle.

In the present procedure, Fmoc-XAL was produced as described in Example 2. The Fmoc-XAL handle was coupled to a Nle-PEG-PS resin (loading: 0.1 mmol/g) using the DIPCDI/HOBt coupling procedure, as described by F. Albericio et al., in *J. Org. Chem.*, 55:3730–3743 (1990). The synthesis of the octapeptide was carried out using Milligen/Biosearch 9050 continuous flow synthesizer (Milligen/Biosearch, Novato, Cailf.). The procedure was performed using the "standard Fmoc protocol" according to the manufacturer's instructions, using 10 equiv. each of Fmoc-amino acid, DIPCDI and HOBt. At the end of each synthesis, cleavage of the peptide from the resin was performed according to the following procedure. The resin-bound peptide was suspended in a cocktail containing 5% trifluoroacetic acid (TFA) and 95% dichloromethane (CH$_2$Cl$_2$) for 1 hour. The mixture was filtered to remove the resin and the filtrate was collected (FIG. 2A). A second cocktail was added to the filtrate, containing 95% TFA and 5% CH$_2$Cl$_2$. After 1 hour of reaction to remove tert-butyl groups (FIG. 2B), two volumes of acetic acid/water (3:7) was added to the mixture, resulting in separation into two phases. The organic (CH$_2$Cl$_2$) phase was removed, and the aqueous (acetic acid) phase was extracted once with CH$_2$Cl$_2$ and lyophilized.

The peptide obtained by this process was analyzed by high performance liquid chromatography (HPLC). The results are shown in FIG. 2B. The yield of the octapeptide was about 90%. Amino Acid Analysis (AAA) was performed, and the results showed the following composition: Thr 1.77, Glu 1.05, Pro 0.96, Gly 1.01, Leu 0.99, Phe 0.98, which is characteristic of the tabanus peptide. The excellent cleavage yield indicates that negligible Trp alkylation took place.

EXAMPLE 4

Preparation of CCK-8 Peptide

The CCK-8 peptide was synthesized as described in Example 4 using the same handle. CCK-8 peptide is difficult to synthesize because it contains two methionine and one tryptophan residues. CCK-8 peptide has the amino acid sequence:

H-Asp-Tyr-Met-Gly-Trp-Met-Asp-Phe-NH$_2$

The cleavage yield of CCK-8 peptide, using a similar procedure with scavengers (thioanisole, anisole and 1,2-ethanedithiol) present in the cleavage cocktail, was about 95%. AAA showed a composition of: Asp 2.03, Gly 1.04, Met 1.92, Tyr 0.99, Phe 1.02, which is characteristic of CCK-8.

EXAMPLE 5

Preparation of CCK-8 Sulfate Peptide

Figure 3:
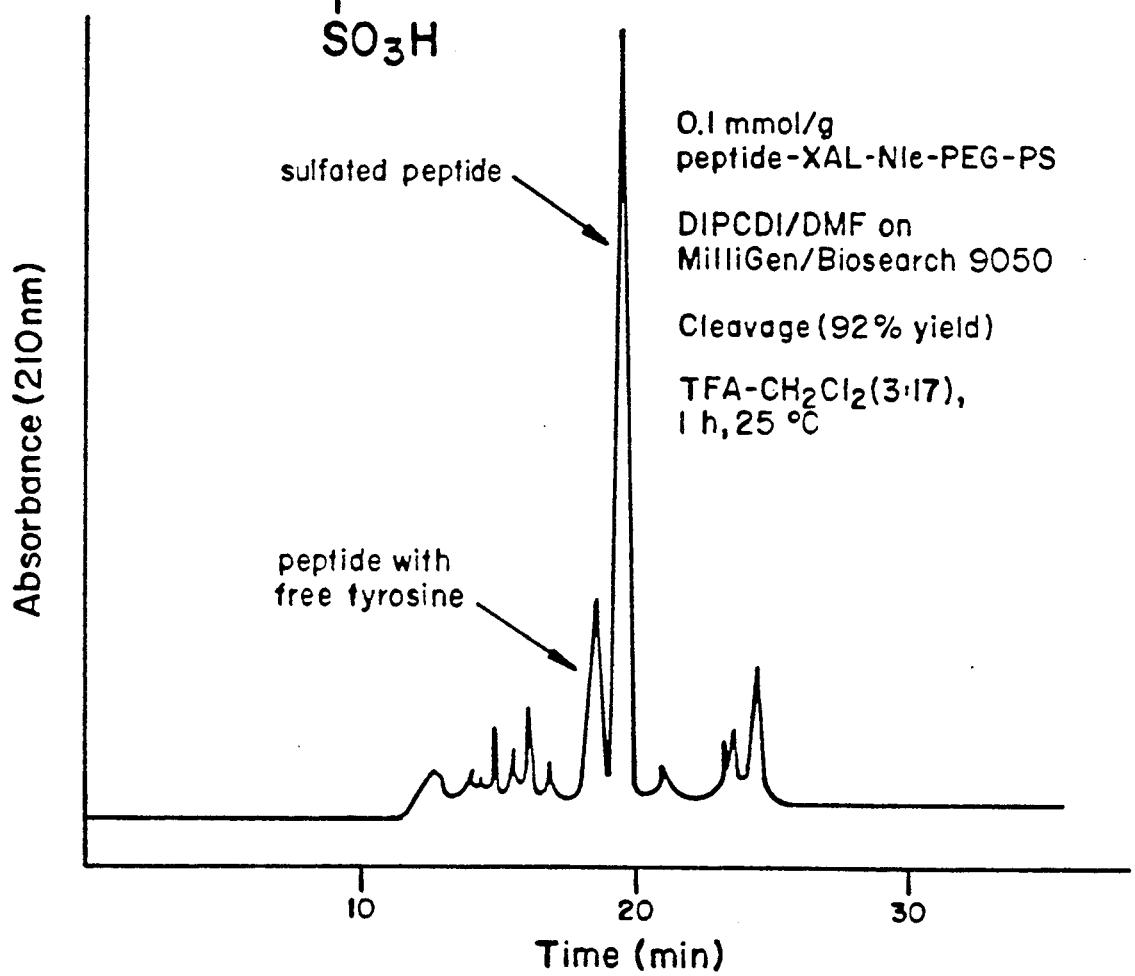
FIG. 3 is an HPLC chromatogram illustrating the results obtained in synthesizing CCK-8 sulfate using the XAL handle.

The CCK-8 sulfate peptide was synthesized according to the procedure described in Example 3. CCK-8 sulfate is very difficult to synthesize because it contains tyrosine sulfate, which is labile to acid. CCK-8 peptide has the same sequence as CCK-8 peptide except that it contains a tyr-sulfate residue in place of the tyr residue of CCK-8. Incorporation of Fmoc-Tyr(SO$_3^-$)—OH$^-$·½Ba$^{+2}$ was carried out manually with BOP/HOBt/NMM on DMF. The remainder of the procedure was the same as set out in Example 4 for CCK-8 except that 15% TFA in CH$_2$Cl$_2$ without scavengers was used. The cleavage HPLC results are shown in FIG. 3. The yield of CCK-8 sulfate peptide was about 92% and AAA showed the following composition:

Asp 2.05, Gly 1.02, Met 1.82, Tyr 0.97, Phe 0.96.

Equivalents

Those skilled in the art will recognize, or be able to ascertain using no more than routine experimentation, many equivalents to the specific embodiments of the invention described herein. Such equivalents are intended to be encompassed by the following claims:

I claim:

1. A xanthenylamide compound bound to a solid support for use in peptide synthesis having the formula:

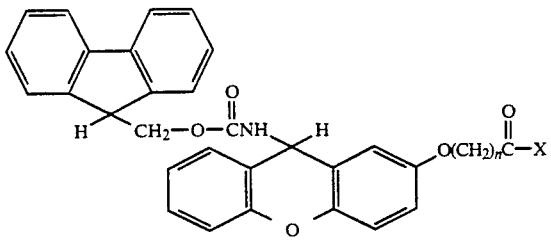

wherein n is an integer from about 1 to about 10; and X is the amino component of an amide linkage that is covalently linked to a solid support.

2. The compound of claim 1 wherein n is 4.

3. The compound of claim 2 wherein the solid support is selected from the group consisting of aminofunctional membranes, polystyrene, polydimethylacrylamides, porous glass, silica, cotton and paper.

4. The compound of claim 3, wherein the polystyrene is selected from the group consisting of aminoacyl polystyrene, aminomethylpolystyrene, p-methylbenzhydrylamine polystyrene and polyethylene glycol-polystyrene.

5. A method of producing an omega-(9-(9-fluorenylmethyloxycarbonyl)aminoxanthan-2-oxy)alkanoic acid derivatives comprising the steps of:

a. alkylating 2-hydroxyxanthone by contacting it the an ω-halo acid or ester under conditions sufficient to cause alkylation to occur;

b. reacting the alkylated hydroxyxanthone with a reducing agent (e.g., sodium borohydride) under conditions sufficient to cause formation of the corresponding xanthydrol; and c. reacting the xanthydrol with 9-fluoroenylmethyl carbamate under conditions sufficient to cause formation of omega-(9-(9-fluorenylmethyloxycarbonyl)aminoxanthan-2-oxy)alkanoic acid derivatives.

6. A method of producing a solid support having a xanthenylamide handle for use in solid-phase peptide synthesis comprising:

a. combining a xanthenyl compound having the general formula:

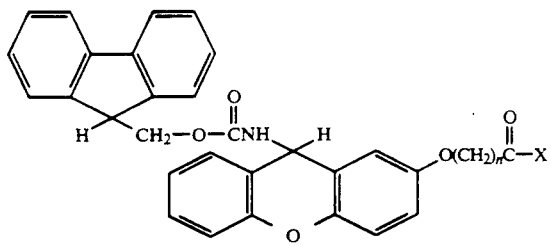

wherein n is from about 1 to about 10, and x is OH or the activating group of an active ester or thioester; with an amino-functionalized solid support; and b. maintaining the combination under conditions sufficient for the carboxyl group on the xanthenyl compound to react with the amino groups on the solid support.

* * * * *